United States Patent [19]

Komano et al.

[11] Patent Number: 4,710,461

[45] Date of Patent: Dec. 1, 1987

[54] PROMOTER DERIVED FROM CHLOROPLAST DNA

[75] Inventors: Tohru Komano, Kyoto; Kanji Ohyma, Uji, both of Japan

[73] Assignees: Kirin Beer Kabushiki Kaisha, Tokyo; Marubeni Kabushiki Kaisha, Osaka, both of Japan

[21] Appl. No.: 642,191

[22] Filed: Aug. 20, 1984

[30] Foreign Application Priority Data

Aug. 24, 1983 [JP] Japan ................................ 58-154270

[51] Int. Cl.⁴ ...................... C12P 21/00; C12N 15/00; C12N 1/00
[52] U.S. Cl. .................................. 435/68; 435/172.3; 435/320; 935/6; 935/29; 935/41; 935/73
[58] Field of Search ...................... 435/172.3, 320, 317, 435/68; 935/6, 41, 73, 29

[56] References Cited

PUBLICATIONS

Grosveld et al, Nature, vol. 295, pp. 120–126 (Jan. 14, 1982).
Ohyama et al, Mol. Gen. Genet., vol. 189, pp. 1–9 (1983).
Maclean et al, Eukaryotic Genes, Their Structure, Activity and Regulation, Butterworths Pub. pp. 410–413 and 460–463 (1983).
Rodriguez et al, Promoters, Structure and Function, Praeger Pub. p. 308 (1982).
Breathnach et al, Ann. Rev. Biochem. vol. 50, pp. 349–383 (1981).
Analects, published by Pharmacia, vol. 13, No. 1 (1985).
In Vitro Gene Fusians . . . , Casadaban et al., J. Bact. 143:971 (1980).
8th Symposium on Plant Tissue Culture, Toyama, Japan, Jul. 19–20, 1983.

*Primary Examiner*—Alvin E. Tanenholtz
*Attorney, Agent, or Firm*—Ladas & Parry

[57] ABSTRACT

A promoter comprises a DNA having the same base sequence as that of a DNA fraction having a size of about 1.1 kbp, which is obtained by cleavage by restriction enzyme Bam HI of a DNA fraction comprising all of a 16SrRNA gene and a part of a 23SrRNA gene, said DNA fraction being obtained by cleavage by restriction enzyme Eco RI of chloroplast DNA of *Marchantia polymorpha* L. The promoter is integrated with a DNA having the same sequence as that of DNA derived from a procaryote into a vector.

13 Claims, 3 Drawing Figures pMC 1403

Eco RI DIGESTION

Eco RI DIGESTION FRAGMENT OF MARCHANTIA POLYMORPHA L CHLOROPLAST

LIGATION AND SCREENING THEREAFTER BY MEANS OF EXPRESSION OF lac Z GENE pMP 903

Bam HI DIGESTION pMC 1403

Bam HI DIGESTION

LIGATION AND SCREENING THEREAFTER BY MEANS OF EXPRESSION OF lac Z GENE pMP 904

4,710,461

PROMOTER DERIVED FROM CHLOROPLAST DNA

BACKGROUND OF THE INVENTION

1. Field of the Invention

The present invention relates to a promoter participating in expression of the function of a structural gene as one moiety or site of a DNA of the gene. More specifically, the present invention relates to a plant-derived promoter.

2. Description of the Prior Art

A promoter is a site of a DNA where an RNA polymerase begins transcription upon being thereon, and the presence of this site is indispensable for expression of a structural gene in an operon to which it belongs.

Analysis of genes has been made mainly on procaryon organisms or procaryotes such as bacteria and phages, particularly bacteria, especially *Escherichia coli*. Hence, promoters of procaryotes have been mainly examined, and many promoters such as a promoter of lac (lactose operon of *E. coli*), a promoter of trp (tryptophan operon of *E. coli*), and a promoter of ara (arabinose operon of *E. coli*) are known.

It is generally considered that a promoter of a eucaryotic cell does not act in a procaryotic cell, and if a procaryote is used as a host in transformation or the like, it is necessary to use a promoter of a procaryote such as a bacterium or phage.

In contrast to the above general knowledge, we have already found that a fraction having a size of about 5.1 kbp among fractions obtained by digestion by or with Eco. RI of a chloroplast DNA of *Marchantia polymorpha* L. that is classified as a eucaryote acts as a promoter in *E. coli* that is a procaryote (8th Symposium of Tissue Culture of Plants). The term "fraction" is herein used interchangeably with a term "fragment".

The intensity of the promoter, that is, the frequency of transcription in forming a RNA from a DNA, or the activity of the promoter, differs with the kind of the promoter, and when DNA containing a promoter is used as a vector for molecular breeding, a promoter having a higher activity is advantageous. Furthermore, since a passenger, namely an exogenous DNA, is integrated in the vector, it is preferable that the size of the promoter be small. Accordingly, a DNA containing a promoter of a small size is easy to use and handle. Therefore, development of a new promoter is always desired.

SUMMARY OF THE INVENTION

The present invention seeks to satisfy the above desire.

More specifically, in accordance with the present invention, there is provided a promoter comprising DNA having the same base sequence as that of a DNA fraction having a size of about 1.1 kbp, which is obtained by digestion by restriction enzyme Bam HI of a DNA fraction comprising all of a 16SrRNA gene and a part of a 23SrRNA gene, the DNA fraction being obtained by digestion by restriction enzyme Eco RI of a chlorplast DNA of *Marchantia polymorpha L*.

The promoter of the present invention, similarly as ordinary promoters, is present as one site of DNA, and the present invention provides an example of such DNA.

More specifically, the hybrid DNA of the present invention comprises the following fractions (A) and (B):

(A) a promoter comprising a DNA having the same base sequence as that of a DNA fraction having a size of about 1.1 kbp, which is obtained by digestion by a restriction enzyme Bam HI of a DNA fraction comprising all of a 16SrRNA gene and a part of a 23SrRNA gene, the DNA fraction being obtained by digestion by restriction enzyme Eco RI of chloroplast DNA of *Marchantia polymorpha* L., and (B) a DNA having the same base sequence as that of a DNA derived from a procaryote.

Moreover, the present invention provides an example of a vector comprising the above-mentioned promoter in it as one site. This vector of the present invention comprises a hybrid DNA containing the above-mentioned fractions (A) and (B).

As will be apparent from the Example given hereinafter, the promoter of the present invention has a high activity. Especially, the promoter of the present invention (1.1 kbp) has a higher activity than the precursor promoter having a size of 5.1 kbp The promotor of the present invention corresponds to a fraction left after removal of about 4/5 upstream portion from the precursor promoter, and it would be unexpected that the activity of the promoter will be improved by this treatment.

Since the promoter of the present invention has a high activity and such a small size of about 1.1 kbp it can be advantageously used in the form of a vector for introduction of an exogenous gene into a procaryote cell (for example, *E. coli*) or a plant cell (for example, protoplast of *Marchantia polymorpha* L.) and manifestation of the exogenous gene in molecular bleeding.

An example of the hybrid DNA of the present invention is plasmid pMP904 formed by integrating this promoter DNA in pMC1403, that is, a plasmid derived from *E. coli*. This hybrid plasmid comprises a pair each of three restricting ehzyme cleavage sites (Bam HI, Eco RI and Sma I) with the promoter of the present invention interposed therebetween, inclusive of the terminal Bam HI and Eco RI cleavage sites of the promoter of the present invention (FIG. 3). Accordingly, a structural gene can easily be introduced into this hybrid plasmid, and this hybrid plasmid can be easily used as a vector. Moreover, cleavage of the promoter of the present invention from this hybrid plasmid and introduction of the promoter thus obtained into another vector can be easily accomplished.

BRIEF DESCRIPTION OF THE DRAWINGS

In the drawings:

In FIG. 2, K, Bg, E and B represent cleavage sites by restriction enzymes Kpn I, Bgl II, Eco RI and Bam HI, respectively, and lac' Z, lac Y and Apr represent a promoter-deficient β-galactsidase gene, a β-galactosidepermease gene and an ampicillin-resistant gene, respectively.

DETAILED DESCRIPTION OF THE INVENTION

Promoter

The promoter of the present invention comprises a DNA having the same base sequence as that of a DNA fraction having a size of about 1.1 kbp, which is obtained by cleavage by restriction enzyme Bam HI of a DNA fraction having all of a 16SrRNA gene and a part of a 23SrRNA gene (hereinafter referred to as "precursor promoter"), this DNA fraction being obtained by cleavage by restriction enzyme Eco RI of chloroplast DNA of *Marchantia polymorpha* L. (Needless to say, kbp is an idiomatic expression indicating $10^3$ base pairs.)

The restriction cleavage map of chloroplast DNA of *Marchantia polymorpha* L. has been disclosed by the present inventors (Mol. Gen. Genet., 189, 1–9, 1983 and the above-mentioned Symposium). This restriction cleavage map is shown in FIG. 1.

Figure 1:
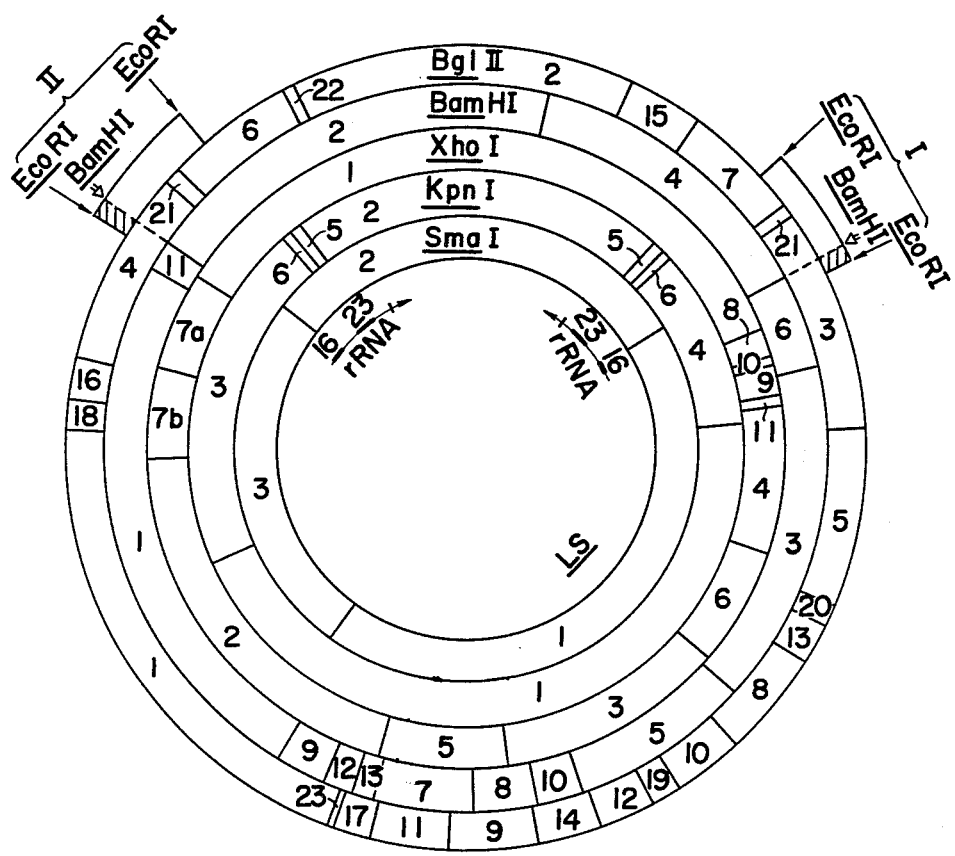
FIG. 1 is a restriction cleavage map of chlorplast DNA of *Marchantia polymorpha* L., which indicates the position of the promoter of the present invention on the map, and in which an rRNA arrow indicates the position and direction of rRNA gene.

The precursor promoter is comprised in regions I and II in FIG. 1. Since this chloroplast DNA has two sets of rRNA genes (16S and 23S) in opposite directions, there are present two sets of the precursor promoter. The DNA in the regions I and II of DNA of *Marchantia polymorpha* L. has a promoter activity, as previously reported by the present inventors (see the above mentioned references).

The promoter of the present invention comprises a DNA having the same base sequence as that of a DNA fraction having a size of about 1.1 kbp, which is obtained by cleavage by restriction enzyme Bam HI of this precursor promoter (having a size of about 5.1 kbp). In the present invention and in interpreting the claims, the expression reading "promoter comprising a DNA having the same base sequence as that of a DNA fraction having a size of about 1.1 kbp " means not only a promoter derived from chloroplast DNA of *Marchantia polymorpha* L. but also a promoter obtained by total chemical synthesis by conventional processes for the synthesis of nucleic acids. (In addition to these two extremities, promoters intermediate therebetween obtained by semichemical synthesis/semibiosynthesis are included).

The promoter of the present invention corresponds to a DNA located at hatched positions in the regions I and II in FIG. 1.

Figure 2:
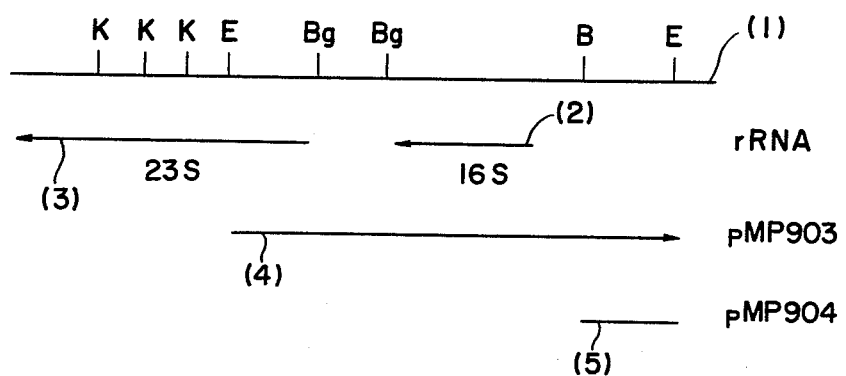
FIG. 2 is a restriction cleavage map of the portion near the base sequence of the promoter of the present invention in chloroplast DNA of *Marchantia polymorpha* L., which illustrates the positions of a DNA fraction of 5.1 kbp and a DNA fraction of 1.1 kbp according to the present invention.

FIG. 2 is an enlarged view of the region I in FIG. 1. Line 1 to which symbols K, E, Bg and B are attached indicates a strand of chloroplast DNA of *Marchantia polymorpha* L. having restriction cleavage sites by restriction enzymes Kpn I, Eco RI, Bgl II and Bam HI, respectively, and a 16SrRNA gene and a 23SrRNA gene are present at positions indicated by lines 2 and 3. The DNA fraction (line 4) obtained by cleavage by Eco RI of this DNA (1) is the precursor promoter having a size of about 5.1 kbp, which contains all of the 16SrRNA gene and a part of the 23SrRNA gene. The promoter of the present invention corresponds to line 5, and this promoter has the restriction cleavage site by Eco RI inherent to the precursor promoter on one end and the newly formed restriction cleavage site by Bam HI on the other end.

Hybrid DNA/Vector

Since a promoter is a DNA fraction present at a certain site of a gene DNA chain, the promoter of the present invention also is ordinarily present in the form of hybrid DNA comprising a fraction of that DNA and a fraction of another DNA. In this case, examples of the fraction of the other DNA are DNA fractions derived from bacteria, viruses, plant cells, mammals and the like and DNA fractions having the same base sequence as that of these DNA fractions.

An example of this hybrid DNA comprises (A) a fraction of the promoter of the present invention and (B) a fraction having the same sequence as that of DNA derived from a procaryote. As described hereinbefore with respect to the promoter of the present invention, by the expression reading "DNA having the same base sequence as that of a DNA derived from a procaryote" is meant not only a DNA derived from that organism but also one obtained by total chemical synthesis. As a preferred instance of the hybrid DNA of this type, one in which at least a part of "DNA derived from a procaryote" comprises at least a plasmid of *E. coli* can be mentioned.

A preferred form of the hybrid DNA comprising the fractions (A) and (B) is a plasmid having a circular structure. An example of this plasmid is pMP904 (described in detail hereinafter) formed by integrating in plasmid pMC1403 derived from *E. coli* the promoter of the present invention and DNA of several base pairs derived from the plasmid. As pointed out hereinbefore, plasmid pMP904 contains a pair each of cleavage sites by three restriction enzymes (E, S and B) with the promoter of the present invention interposed therebetween and is advantageous.

The above mentioned hybrid DNA or plasmid comprising the promoter of the present invention can be utilized as a vector for introducing exogenous DNA into an appropriate host cell through a recombinant having the exogenous DNA inserted therein. In one example of the vector, the fraction other than the promoter of the present invention is a DNA having the same base sequence as that of a DNA derived from a procaryote. That is, the vector of the present invention comprises a hybrid DNA comprising the above mentioned fractions (A) and (B). An example of the vector of this type is a vector in which DNA derived from a procaryote comprises at least a part of the plasmid of *E. coli* and/or a vector in the form of a plasmid having a circular structure. One example of this plasmid is pMP904 (described in detail hereinafter).

*E. coli* K12 MC1061 containing plasmid pMP904 was deposited with the Fermentation Research Institute of the Agency of Industrial Science and Technology, and the deposition number FERM BP-562 has been assigned.

Utility of Promoter of Present Invention

The promoter of the present invention has a utility inherent in promoters similarly as the precursor promoter or other ordinary promoters.

More specifically, a chimera or recombinant DNA or plasmid obtained by bonding a gene of a procaryote to the downstream portion (the side of cleavage by Eco RI) of the promoter of the present invention (ordinarily in the form of hybrid DNA or hybrid plasmid) is advantageously utilized for expression of that gene in an appropriate host cell.

Ordinarily, in the expression of genes of a procaryote, for example in the case of lactose operon, one promoter dominates the expression of a series of subsequent structural genes. In contrast, in the expression of genes of a eucaryote, a promoter is necessary for each gene, and expression of an exogenous gene derived from a eucaryotic cell is made possible if a promoter is located before the gene. Accordingly, if the DNA base sequence of the promoter of the present invention is determined, the promoter of the present invention can be effectively used for the expression of genes of a eucaryote by bonding the exogenous DNA fraction to an integration site downstream of an initiation codon on the DNA fraction of the promoter of the present invention.

Formation of Promoter/Hybrid Plasmid

The promoter of the present invention is prepared according to a process comprising in principle isolation of chloroplast DNA of *Marchantia polymorpha* L. and a two-step restriction enzyme treatment. Preferably, the promoter of the present invention is prepared by selecting an appropriate plasmid and appropriately performing unit operations such as restriction cleavage, ligation and transformation to obtain the promoter in the form of a recombinant with the plasmid. These unit operations are conventionally performed and are described in detail in references, for example, "Experimental Manual of Genetic Manipulations" (published by Kodansha, 1982), or "Molecular Cloning-A Laboratory Manual" (published by Cold Spring Harbor Laboratory, 1982). If the base sequence of this promoter is known, the promoter can be produced by total synthesis.

As pointed out hereinbefore, the precursor promoter (having a size of about 5.1 kbp of the promoter of the present invention is known. An embodiment of the process for preparing this precursor promoter and the promoter of the present invention in the form of a hybrid plasmid will now be described with reference to FIG. 3 illustrating the reaction steps of this process.

Figure 3:
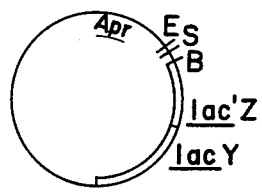
FIG. 3 is a diagram illustrating a process for the preparation of the promoter of the present invention.
Figure 3:
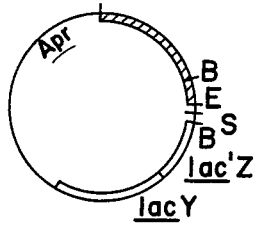
Figure 3:
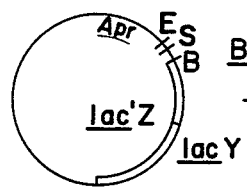
Figure 3:
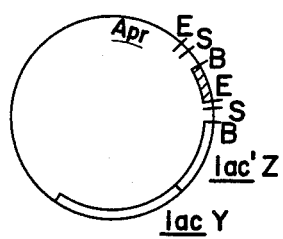

Referring to FIG. 3, plasmid pMP903 comprises a fraction (hatched portion) of the precursor promoter (having a size of about 5.1 kbp), and plasmid pMP904 comprises a fraction (hatched portion) of the promoter of the present invention (having a size of about 1.1 kbp). Incidentally, plasmid pMC1403 comprises structural gene lac Z but is deficient in the promoter region [J. Bacteriol., 143, No.2, pages 971-980 (1980)].

(i) Preparation of Plasmid pMP903

Chloroplast DNA is isolated and purified from cultured cells of *Marchantia polymorpha* L. in the stationary stage according to the method of Ohyama et al [Agric. Biol. Chem., 46, 137 (1982)]. This DNA is digested by restriction enzyme Eco RI. Separately, plasmid pMC1403 of *E. coli* (which has structural gene lac Z but is deficient in the promoter region) is digested by restriction enzyme Eco RI and subjected to an alkaline phosphatase treatment. These DNA's are ligated by T4 ligase. By the formed recombinant plasmid, *E. coli* MC1061 (lac−) is transformed, and on a MacConkey agar culture medium containing ampicillin (J. H. Miller; Experiments in Molecular Genetics, Cold Spring Harbor, 1972, page 48), an ampicillin-resistant recombinant having a β-galactosidase activity is obtained. When the plasmid of this recombinant is extracted and the structure is examined, a restriction cleavage map, as shown in the middle portion of FIG. 3, is obtained. It is seen that there is contained a fraction of chloroplast DNA of *Marchantia* polymorpha L., which has a size of about 5.1 kbp.

(ii) Presumption of Position of Promoter-Containing Fraction of 5.1 kbp Formed by Digestion by Eco RI in Cleavage Map of Chloroplast DNA of *Marchantia polymorpha* L.

The position of the fraction formed by digestion by Eco RI is found to be a known ribosomal RNA gene containing position on chloroplast DNA of *Marchantia polymorpha* L. according to the method using this fraction as a probe. From the detailed restriction cleavage map (FIG.1) of chloroplast DNA of *Marchantia polymorpha* L., it is seen that the above position is in the regions I and II in FIG. 1. Since it is known that these regions are in opposite directions, the same base sequence appears at two points as shown in FIG. 1.

(iii) Preparation of Plasmid pMP904

The plasmid pMP903 thus obtained is cleaved by restriction enzyme Bam HI. Separately, plasmid pMC1403 is digested by restriction enzyme Bam HI and subjected to an alkaline phosphatase treatment. These DNA's are ligated by T4 ligase, and *E. coli* MC1061 is transformed by the recombinant formed. On a MacConkey culture medium, an ampicillin-resistant recombinant having a β-galactosidase activity is obtained. A plasmid different from the starting plasmid pMP903 is obtained in the recombinant. The restriction cleavage map of this plasmid is as shown in the lower portion of FIG. 3. This plasmid, namely, pMP904, comprises a fraction of 1.1 kbp formed by cleavage by Bam HI-Eco RI of chloroplast DNA of *Marchantia polymorpha* L., that is, the promoter of the present invention.

EXPERIMENTAL EXAMPLE

EXAMPLE (1) Recovery of Chloroplast DNA

Cells of Marchantia polymorpha L. were cultured at 25° C. for 5 days in 2 liters of a 1M51C culture medium [Plant Sci. Lett., 14, 225 (1979)]. The cells were collected and homogenized by a French press, and a crude chloroplast fraction was collected according to customary procedures. The crude chloroplast fraction was fractionated by 20% and 40% two-layered sucrose density gradient centrifugation to obtain a chloroplast fraction. The chloroplast fraction was dissolved in a TE buffer solution (10 mM tris-hydrochloride buffer solution - 1 mM EDTA) (pH 8.0) containing 3% of Sarkosyl NL97 and fractionated by cesium chloride density gradient centrifugation to obtain 30 ug of closed circular chloroplast DNA.

(2) Construction of pMP903

One of this chloroplast DNA was reacted with 10 units of Eco RI in a solution comprising 10 mM tris-hydrochloride buffer solution (pH 7.6), 7 mM magnesium chloride, 100 mM sodium chloride and 7 mM 2-mercaptoethanol for 1 hour at 37° C., which reaction was followed by phenol treatment and precipitation with ethanol.

Separately, 1 μg of plasmid pMC1403 was cleaved by Eco RI under the same conditions as described above, after which phenol treatment and precipitation with ethanol were carried out. The precipitate was dissolved in a TE buffer solution (pH 8.0), and, with addition of 1 unit of an *E. coli* alkaline phosphatase to the solution, reaction was carried out at 37° C. for 30 minutes, followed by phenol treatment and precipitation with ethanol.

The thus treated chloroplast DNA fraction and plasmid pMC1403 DNA were dissolved in water, and bonding reaction was carried out. In 50 μl of the reaction liquid, there were contained 1 mM ATP-66 mM trishydrochloride buffer solution (pH 7.6), 6.6 mM magnesium chloride, 20 mM dithiothreitol and 0.1 unit of T4 ligase. Reaction was carried out at 12° C. for 16 hours, followed by phenol treatment and precipitation with ethanol. The precipitate was dissolved in 10 μl of TE (pH 8.0).

Transformation of E. coli MC1061 (lac−) was performed by using the total amount of the solution according to the calcium method where E. coli was converted to competent cells. The DNA prepared according to the above described method was added to the competent cells, and the mixutre was kept at 0° C. for 20 minutes and then heated at 43.5° C. for 2 minutes. The treated mixture was mixed with the same amount of a 2 × L culture medium (a solution of a pH of 7.5, formed by dissolving 20 g of polypeptone, 10 g of yeast extract and 10 g of NaCl in 1 liter of water), and incubation was carried out at 37° C. for 60 minutes. The incubation product was scattered onto a MacConkey agar culture medium containing 50 mg/liter of ampicillin (formed by dissolving 10 g of the culture medium supplied by Difco Co. in 100 ml of water). Stationary culturing was carried out overnight at 37° C. to obtain 200 ampicillin-resistant strains, 3 strains of which formed a red colony. This plasmid was extracted according to the alkali method and was cleaved by restriction enzymes Eco RI, Bam HI, Sma I and Bgl II to form a restriction cleavage map (see FIG. 3). As shown in FIG. 3, it was found that a fraction of chloroplast DNA of Marchantia polymorpha L. having a size of 5.1 kbp was inserted into the lite of cleavage by Eco RI in plasmid pMC1403. The thus obtained plasmid was designated as pMP903.

(3) Construction of pMP904

It was revealed by the present inventors that a fraction of chloroplast DNA of Marchantia polymorpha L. having a size of 5.1 kbp is comprised in plasmid pMP903, and RNA transcription is initiated from this DNA fraction to produce β-galactosidase (8th Symposium of Tissue Culture of Plants).

In order to further limit this promoter site, pMP904 was prepared. That is, after plasmid pMP903 was recovered by the alkali method, 1 μg of the DNA was digested by 10 units of Bam HI according to the procedure described above. Separately, 1 μg of plasmid pMC1403 was similarly decomposed by 10 units of Bam HI and then subjected to alkaline phosphatase treatment.

These DNA fractions were ligased by T4 ligase, and transformation of E. coli MC1061 was carried out by the formed recombinant plasmid to obtain 100 clones as amicillin-resistant strains, 16 clones of which had a β-galactosidase activity. Three clones among these active clones contained a fraction of chloroplasmid DNA of Marchantia polymorpha L. having a size of 1.1 kbp (the remaining clones being the same as plasmid pMP903). This plasmid was extracted and a restriction cleavage map was formed (the lower portion of FIG. 3).

This plasmid was named "pMP904". It was considered that the promoter is present in the fraction of 1.1 kbp surrounded by Eco RI and Bam HI.

REFERENTIAL EXAMPLE

A recombinant of the DNA fraction of 1.1 kbp comprising the promoter of the present invention and a plasmid comprising a β-galactosidase gene was prepared. It was clarified that the present promoter was effective for expression of β-galactosidase and had an activity about 1.2 times the activity of a lactose promoter and the activity of the promoter in a fraction having a size of about 5.1 kbp.

More specifically, the β-galactosidase-producing activity of the strain obtained by transformation with plasmid pMC904 (obtained in the Example) of E. coli having no β-galactosidase gene was compared with those of (1) E. coli, wild strain W3110, capable of producing β-galactosidase by a lactose promoter, (2) non-transformed E. coli MC1061, (3) a strain formed by transformation of E. coli MC1061 with plasmid pMC1403 having a β-galactosidase gene but having no promoter, and (4) a strain formed by transformation of E. coli MC1061 with recombinant plasmid pMC903 comprising a DNA fraction having a size of 5.1 kbp and a β-galactosidase gene. The β-galactosidase-producing activity of each strain was measured according to the Miller method (J. H. Miller; Experiments in Molecular Genetics, Cold Spring Harbor, 1972, page 352).

The results obtained are shown in Table 1.

TABLE 1

Production of β-Galactosidase by Promoter of Present Invention (in E. coli)

| Host | Plasmid | β-Galactosidase Activity (units) | |
|---|---|---|---|
| | | IPTG* Added | IPTG Not Added |
| W3110 (lac+) | — | 338 | 11 |
| MC1061 (Δlac Z) | — | 0 | 0 |
| MC1061 (Δlac Z) | pMC1403 (lac' Z) | 0 | 0 |
| MC1061 (Δlac Z) | pMP903 | — | 336 |
| MC1061 (Δlac Z) | pMC904 | — | 404 |

*Note:
IPTG: isopropylthiogalactoside

From the above results, it will readily be understood that since the DNA fraction of 1.1 kbp DNA comprising the promoter of the present invention acts as a promoter even if it is integrated into recombinant DNA and since this DNA fraction has a β-galactosidase-producing activity about 1.2 times that of the lactose promoter and the DNA fraction of 5.1 kbp, the DNA fraction of 1.1 kbp comprising the promoter of the present invention is of high value.

What is claimed is:

1. A promoter comprising a DNA having the same base sequence as that of a DNA fraction having a size of about 1.1 kbp, which is obtained by cleavage by restriction enzyme Bam HI of a DNA fraction comprising all of a 16SrRNA gene and a part of a 23SrRNA gene, said DNA fraction comprising all of a 16SrRNA gene and a part of a 23SrRNA gene being obtained by cleavage by restriction enzyme Eco RI of chloroplast DNA of Marchantia polymorpha L; said promoter being isolated from the rest of the chloroplast DNA of Marchantia polymorpha L.

2. A hybrid DNA comprising the following fractions (A) and (B):
(A) a promoter comprising a DNA having the same base sequence as that of a DNA fraction having a size of about 1.1 kbp, which is obtained by cleavage by restriction enzyme Bam HI of a DNA fraction comprising all of a 16SrRNA gene and a part of a 23SrRNA gene, said DNA fraction comprising all of a 16SrRNA gene and a part of a 23SrRNA gene being obtained by cleavage by restriction enzyme Eco RI of chloroplast DNA of *Marchantia polymorpha* L., and said promoter being isolated from the rest of the chloroplast DNA of *Marchantia polymorpha* L; and (B) A DNA having the same base sequence as that of DNA derived from a procaryote.

3. A vector comprising a hybrid DNA comprising the following fractions (A) and (B):

(A) a promoter comprising a DNA having the same base sequence as that of a DNA fraction having a size of about 1.1 Kbp, which is obtained by cleavage by a restriction enzyme Bam HI of a DNA fraction comprising all of a 16SrRNA. gene and a part of a 23SrRNA gene, said DNA fraction comprising all of a 16SrRNA. gene and a part of a 23SrRNA gene being obtained by cleavage by restriction enzyme Eco RI of chloroplast DNA of *Marchantia polymorpha* L., and said promoter being isolated from the rest of the chloroplast DNA of *Marchantia polymorpha* L; and (B) a DNA having the same sequence as that of DNA. derived from a protarugate.

4. A hybrid DNA as in claim 9 wherein the DNA derived from a procaryote is one which comprises at least a part of a plasmid of *Escherichia coli*.

5. A hybrid DNA as in claim 2 which is in the form of a plasmid.

6. A vector as in claim 3 wherein the DNA derived from a procaryote is one which comprises at least a part of a plasimid of *Escherichia coli*.

7. A vector as in claim 3 which is in the form of a plasmid.

8. A promoter as in claim 1, wherein said promoter has a higher promoter activity in *E. coli*, which is a procaryote, than that of said DNA fraction comprising all of a 16SrRNA gene and part of a 23SrRNA. gene.

9. A hybrid DNA as in claim 2, wherein said promoter has a higher promoter activity in *E. coli*, which is a procaryote, than that of said DNA fraction comprising all of a 16SrRNA gene and part of a 23SrRNA gene.

10. A vector as in claim 3, wherein said promoter has a higher promoter acitvity in *E. coli*, which is a procaryote, than that of said DNA fraction comprising all of a 16SrRNA gene and part of a 23SrRNA gene.

11. A method for achieving expression of DNA having the same sequence as that of DNA derived from a eukaryote in a prokaryotic host cell, comprising transforming said host cell with a vector comprising (A) a promoter comprising a DNA having the same base sequence as that of a DNA fraction having a size of about 1.1 Kbp, which is obtained by cleavage by a restriction enzyme Bam HI of a DNA fraction comprising all of a 16SrRNA. gene and a part of a 23SrRNA. gene, said DNA fraction comprising all of a 16SrRNA gene and a part of a 23SrRNA gene being obtained by cleavage by restriction enzyme Eco RI of chloroplast DNA of *Marchantia polymorpha* L. which is a eukaryote, said promoter being isolated from the rest of the chloroplast DNA of *Marchantia polymorpha* L.

(B) a DNA having the same sequence as that of DNA derived from a procaryote, and permitting expression said eukaryotic promoter in said prokaryotic host.

12. A method as in claim 11, wherein the DNA derived from a procaryote is one which comprises at least a part of a plasmid of *Escherichia coli*.

13. A method as in claim 11 wherein said vector is in the form of a plasmid.

* * * * *